(12) United States Patent
Zhang

(10) Patent No.: US 9,192,315 B2
(45) Date of Patent: Nov. 24, 2015

(54) PATIENT SIGNAL ANALYSIS AND CHARACTERIZATION BASED ON LATE POTENTIALS

(71) Applicant: Siemens Medical Solutions USA, Inc., Malvern, PA (US)

(72) Inventor: Hongxuan Zhang, Palatine, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 0 days.

(21) Appl. No.: 14/269,574

(22) Filed: May 5, 2014

(65) Prior Publication Data

US 2014/0364753 A1    Dec. 11, 2014

Related U.S. Application Data

(60) Provisional application No. 61/831,227, filed on Jun. 5, 2013.

(51) Int. Cl.
A61B 5/0472    (2006.01)
A61B 5/04    (2006.01)

(52) U.S. Cl.
CPC ............ *A61B 5/04014* (2013.01); *A61B 5/0472* (2013.01)

(58) Field of Classification Search
None
See application file for complete search history.

(56) References Cited

U.S. PATENT DOCUMENTS

| | | |
|---|---|---|
| 4,721,114 A | 1/1988 | Dufault et al. |
| 4,802,491 A | 2/1989 | Cohen et al. |
| 5,215,099 A | 6/1993 | Haberl et al. |
| 5,782,876 A | 7/1998 | Flammang |
| 5,810,722 A | 9/1998 | Heikkilae |
| 6,128,526 A | 10/2000 | Stadler et al. |
| 6,169,919 B1 | 1/2001 | Nearing et al. |
| 6,266,561 B1 | 7/2001 | Gliner |
| 6,280,391 B1 | 8/2001 | Olson et al. |
| 6,304,772 B1 | 10/2001 | Taha et al. |
| 6,480,733 B1 | 11/2002 | Turcott |
| 6,501,983 B1 | 12/2002 | Natarajan et al. |
| 6,609,023 B1 | 8/2003 | Fischell et al. |
| 6,785,573 B2 | 8/2004 | Kovtun et al. |
| 6,819,953 B2 | 11/2004 | Yonce et al. |
| 6,850,796 B1 | 2/2005 | Mortara |
| 6,947,789 B2 | 9/2005 | Selvester et al. |
| 7,066,891 B2 | 6/2006 | Stadler et al. |
| 7,181,268 B2 | 2/2007 | Sheldon et al. |
| 7,270,662 B2 | 9/2007 | Visram et al. |
| 7,277,745 B2 | 10/2007 | Natarajan et al. |
| 7,386,340 B2 | 6/2008 | Schlegel et al. |
| 7,412,283 B2 | 8/2008 | Ginzburg et al. |
| 7,539,535 B1 | 5/2009 | Schlegel et al. |
| 7,542,794 B1 | 6/2009 | Zhang et al. |
| 7,996,084 B2 | 8/2011 | Stylos et al. |
| 8,126,549 B2 | 2/2012 | Sigg et al. |
| 8,233,972 B2 | 7/2012 | Zhang |
| 8,265,740 B2 | 9/2012 | Fischell et al. |
| 8,275,457 B1 | 9/2012 | Fischell et al. |
| 8,364,248 B2 | 1/2013 | Zhang |
| 2005/0004481 A1* | 1/2005 | Xue et al. ...................... 600/509 |

* cited by examiner

*Primary Examiner* — Kennedy Schaetzle

(57) ABSTRACT

Disclosed herein is a framework for facilitating patient signal analysis. In accordance with one aspect, patient signal data including at least one identified cycle is segmented into at least two regions of interest, including a late potential region of interest. The late potential region of interest may be an RS, RT, S-full or T-full signal portion. At least one patient signal parameter is determined based at least in part on the segmented regions of interest. A pathology or event may be detected based on the determined patient signal parameter.

21 Claims, 8 Drawing Sheets

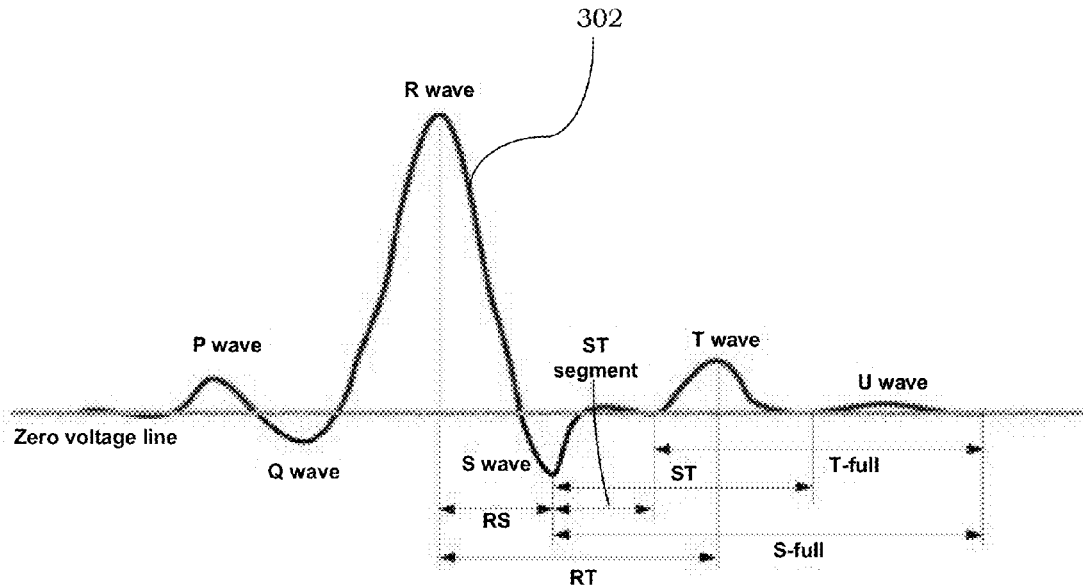

| Signal name | Signal portion and functional segmentation |
|---|---|
| RS | Late depolarization of the ventricular activity |
| ST segment | Gold standard; Early repolarization of the ventricular activity |
| ST | Typical whole ventricular repolarization and later potentials if U wave is negligible |
| RT | Main portion of myocardial ischemia signal effecting signal portion in the cardiac cycle, from peak time of ventricular depolarization to peak time of ventricular repolarization |
| S-full | Functional full ventricular repolarization and later potentials including U wave |
| T-full | Functional full late repolarization (T wave) and later potentials including U wave |

Table 1

*Fig. 3*

| Mapping position and location | Calculation methods | Normal healthy | Early ischemia | Late ischemia (early infarction) |
|---|---|---|---|---|
| P1 | ST segment elevation (mV) | 0.00 | 0.01 | 0.07 |
| | Time-frequency distribution area ratio | 2.0 | 3.5 | 4.5 |
| P2 | ST segment elevation (mV) | 0.00 | 0.01 | 0.08 |
| | Time-frequency distribution area ratio | 2.1 | 4.1 | 6.1 |
| P3 | ST segment elevation (mV) | 0.00 | 0 | 0.05 |
| | Time-frequency distribution area ratio | 2.1 | 3.7 | 4.6 |
| P4 | ST segment elevation (mV) | 0.00 | 0 | 0.04 |
| | Time-frequency distribution area ratio | 2.0 | 3.1 | 3.9 |

*Fig. 8*

PATIENT SIGNAL ANALYSIS AND CHARACTERIZATION BASED ON LATE POTENTIALS

CROSS-REFERENCE TO RELATED APPLICATIONS

This application claims the benefit of U.S. provisional application No. 61/831,227 filed on Jun. 5, 2013, the entire contents of which are incorporated herein by reference.

TECHNICAL FIELD

The present disclosure generally relates to systems and methods for analyzing and characterizing patient signals based on late potentials.

BACKGROUND

Cardiac arrhythmia is a condition in which the electrical activity of the heart is irregular or faster or slower than normal. Cardiac arrhythmia may be classified by rate and/or mechanism. For instance, atrial fibrillation (AF) is the most common type of serious arrhythmia that involves a very fast and irregular contraction of the atria. Ventricular fibrillation (VF) is a condition in which there is uncoordinated contraction of the cardiac muscle of the ventricles in the heart. Myocardial ischemia is a type of arrhythmia that occurs when blood flow to the heart muscle is decreased by a partial or complete blockage of the heart's arteries. Myocardial infarction (commonly known as a heart attack) occurs when blood stops flowing properly to part of the heart and the heart muscle is injured due to not receiving enough oxygen. This can lead to irreversible scarring and necrosis of the muscle tissue, reducing the efficiency with which the heart can pump blood to the rest of the body and possibly leading to fatal cardiac arrhythmia.

Cardiac functional abnormality and arrhythmia usually slow down tissue performance (e.g., contracting and reperfusion) and reduce blood flow to regions of the heart. Cells respond by altering the action potentials. The changes in these individual cells manifest in electrograms during depolarization and repolarization, reducing signal energy (hyperkalemia or anoxia) or creating multi-phasic waveform, particularly distortions in the electrophysiological response morphology. Electrophysiological (EP) response and activity analysis is routinely used to manage such cardiac arrhythmias, disorders and irregularities. The 12-lead electrocardiogram (ECG) and multi-channel intra-cardiac electrograms (ICEG) are generally regarded as the diagnostic reference standard for evaluating cardiac rhythm and events.

Early myocardial ischemia and infarction (MI) analysis and characterization are critical for the management of cardiac disorders and irregularities. Usually, surface ECG signal analyses based on electrophysiological activity waveforms (e.g., ECG signals and intra-cardiac electrograms) and time domain parameters (e.g., magnitude voltage) of the waveforms are utilized for detecting cardiac arrhythmia and diagnosing pathology. Known systems use ECG waveform analysis of a P wave, QRS complex, ST segment and T wave, to monitor and identify cardiac arrhythmia.

However, known methods based on waveform morphology and time domain parameter analysis are often subjective and time-consuming, and require expertise and clinical experience for accurate interpretation and proper cardiac rhythm management. Known systems typically fail to provide sufficient information on cardiac electrophysiological function/activity interpretation, tissue mapping and arrhythmia localization. Additionally, known cardiac detection methods often focus on time (e.g., amplitude, latency) or frequency (e.g., power, spectrum) domain changes in an ECG signal, which may not detect small signal changes that are usually invisible in a signal wave morphology display. Further, known systems fail to provide quantitative clinical evaluation of myocardial ischemia events.

Accordingly, there exists a need to provide an improved framework to address these deficiencies and related problems.

SUMMARY

The present disclosure relates to a framework for facilitating patient signal analysis. In accordance with one aspect, patient signal data including at least one identified cycle is segmented into at least two regions of interest, including a late potential region of interest. The late potential region of interest may be an RS, RT, S-full or T-full signal portion. At least one patient signal parameter is determined based at least in part on the segmented regions of interest. A pathology or event may be detected based on the determined patient signal parameter.

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

FIG. 3 illustrates an exemplary waveform segmentation method;

FIG. 8 shows a table for comparing exemplary multichannel signal changes for myocardial ischemia diagnosis.

DETAILED DESCRIPTION

Figure 1:
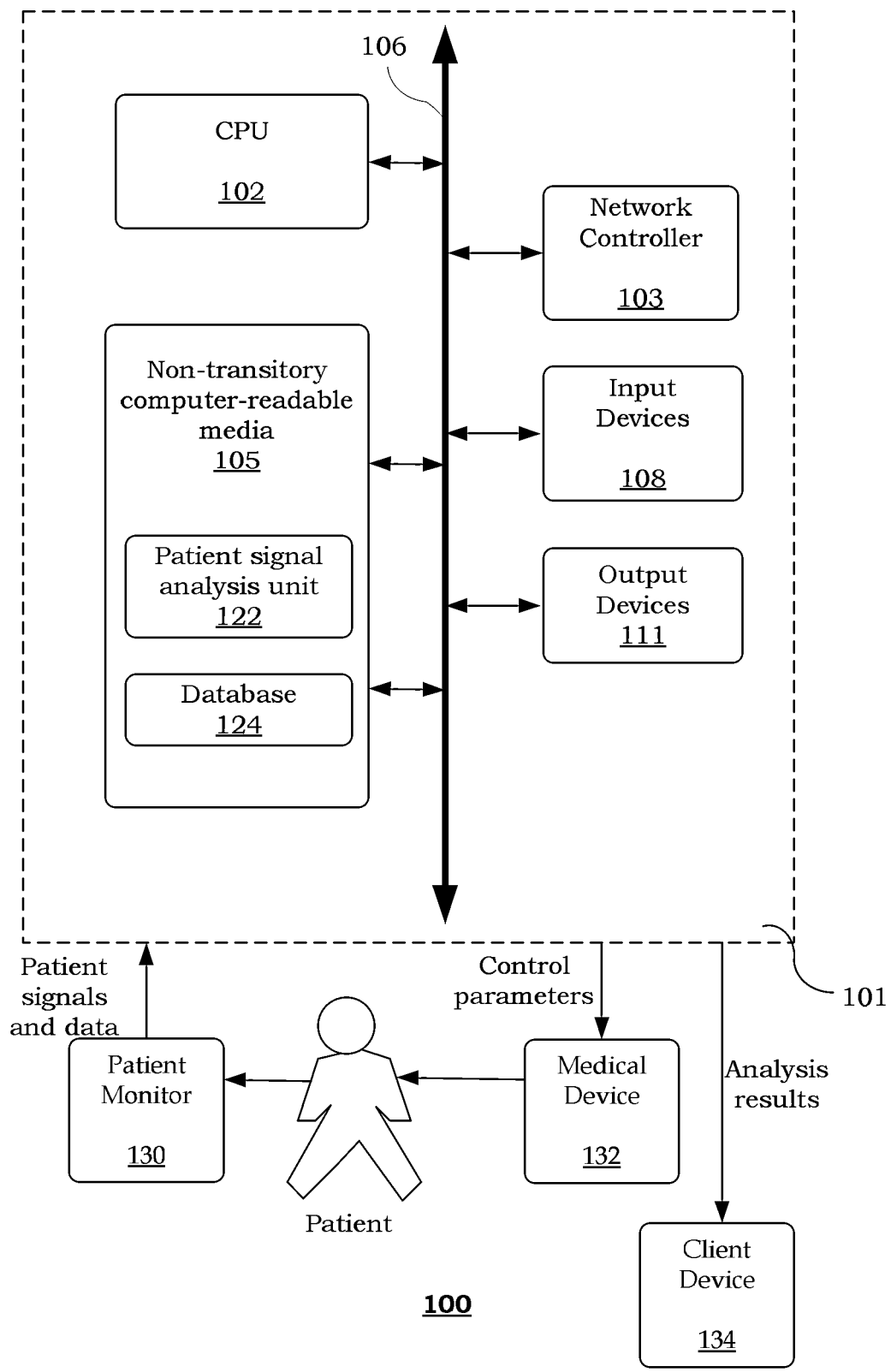
FIG. 1 shows an exemplary system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

It is to be understood that the system and methods described herein may be implemented in various forms of hardware, software, firmware, special purpose processors, or a combination thereof. Preferably, the present invention is implemented in software as an application (e.g., n-tier application) comprising program instructions that are tangibly embodied on one or more program storage devices (e.g., magnetic floppy disk, RAM, CD ROM, ROM, etc.), and executable by any device or machine comprising suitable architecture. If written in a programming language conforming to a recognized standard, sequences of instructions designed to implement the methods can be compiled for execution on a variety of hardware platforms and for interface to a variety of operating systems. In addition, embodiments of the present framework are not described with reference to any particular programming language. It will be appreciated that a variety of programming languages may be used to implement embodiments of the present invention.

It is to be further understood that since the constituent system modules and method steps depicted in the accompanying Figures are preferably implemented in software, the actual connections between the system components (or the flow of the process steps) may differ depending upon the manner in which the present invention is programmed. Given the teachings herein, one of ordinary skill in the related art will be able to contemplate these and similar implementations or configurations of the present invention.

The present disclosure provides a framework to analyze patient signals. Examples of patient signals include cardiac electrophysiological signals, such as surface ECG and intracardiac electrograms (ICEG) signals. In accordance with some implementations, late potential portions of the patient signals are segmented and categorized to facilitate late potential pattern diagnosis, characterization and/or mapping. Late potential signal ratios, variations and/or distributions may be derived from the segmented late potential signal portions to advantageously capture minute changes in amplitude or energy distribution that are associated with, for example, early stages of coronary artery disease (especially for myocardial ischemia and infarction), which facilitate early diagnosis and treatment of patients. By analyzing distortion and change in selected late potential signal portions and/or areas, the location, timing, severity, type and/or other characteristics of cardiac function, pathologies and/or diseases may be more precisely and reliably diagnosed, detected, mapped and/or characterized. These and other features and advantages will be described in more detail herein.

For purposes of illustration, the present framework is described herein in the context of electrocardiography signal analysis for heart function characterization, detection and/or diagnosis. However, it should be appreciated that the present framework is also useful for analyzing other types of electrophysiological signals originating from other parts of the body, including but not limited to, the brain, muscles, eyes, auditory system and so forth. In addition, the present framework may also be used for analysis of other types of patient signals, including capnograph waveforms, saturation of peripheral oxygen (SPO2) signals, blood pressure signals, etc.

FIG. 1 shows an exemplary system 100 for implementing the present framework.

It is to be understood that, because some of the constituent system components and method steps depicted in the accompanying figures can be implemented in software, the actual connections between the systems components (or the process steps) may differ depending upon the manner in which the present framework is programmed. For example, the system 100 may be implemented in a client-server, peer-to-peer (P2P) or master/slave configuration. In such configurations, the system 100 may be communicatively coupled to other systems or components via a network, such as an Intranet, a local area network (LAN), a wide area network (WAN), a P2P network, a global computer network (e.g., Internet), a wireless communications network, or any combination thereof.

As shown in FIG. 1, the exemplary system 100 includes a computer system 101, a patient monitor 130, a medical device 132 and a client device 134. The computer system 101 may include, inter alia, a central processing unit (CPU) 102, a non-transitory computer-readable media 105, one or more output devices 111 (e.g., printer, display monitor, projector, speaker, etc.), a network controller 103, an internal bus 106 and one or more input devices 108, for example, a keyboard, mouse, touch screen, gesture and/or voice recognition module, etc. Computer system 101 may further include support circuits such as a cache, a power supply, clock circuits and a communications bus. Various other peripheral devices, such as additional data storage devices and printing devices, may also be connected to the computer system 101.

The present technology may be implemented in various forms of hardware, software, firmware, special purpose processors, or a combination thereof, either as part of the microinstruction code or as part of an application program or software product, or a combination thereof, which is executed via the operating system. In one implementation, the techniques described herein may be implemented as computer-readable program code tangibly embodied in one or more non-transitory computer-readable media 105. Non-transitory computer-readable media 105 may include random access memory (RAM), read-only memory (ROM), magnetic floppy disk, flash memory, and other types of memories, or a combination thereof. The present techniques may be implemented by patient signal analysis unit 122 that is stored in computer-readable media 105. As such, the computer system 101 is a general-purpose computer system that becomes a specific purpose computer system when executing the computer-readable program code. The same or different computer-readable media 105 may be used for storing a database 124. Database 124 may include a repository of determined patient signal parameters, selectable predetermined functions, calculation parameters (e.g., thresholds), patient signal data, (e.g., electrophysiological, SPO2, respiration signal data, etc.), patient data (e.g., demographic data, pathology history, etc.), patient status reports, other input data, other determined output parameters, or a combination thereof.

Patient signal data may be provided by a patient monitor 130 that is communicatively coupled to the computer system 101. Patient monitor 130 may be used to acquire various types of patient biometric or physiological signal data for monitoring the patient. For example, the monitoring information may include, but is not limited to, electrophysiological signal data (e.g., ECG, ICEG, etc.), SPO2 signal data, respiration signal data, blood pressure, temperature and/or other patient biometric, physiological or medical parameter information. The patient monitor 130 may include appropriate biometric sensors (e.g., multiple leads for surface ECG and catheter for intra-cardiac electrograms) for acquiring the patient signal data.

Computer system 101 may further be communicatively coupled to medical device 132 to provide control parameters for manipulating treatment of the patient. Medical device 132 may include, for example, a pacing stimulator or pacemaker, ablator, defibrillator (e.g., implantable cardioverter defibrillator or ICD), and so forth. Computer system 101 may implement a closed loop feedback analysis and control framework that adaptively and automatically adjusts control parameters used to manipulate treatment via medical device 132.

Computer system 101 may further be communicatively coupled to client device 134 to provide results of the patient signal analysis. Such results may be presented in the form of warnings, recordings, reports, etc., at the client device 134. Client device 134 may include components similar to the computer system 101, and may be in the form of a desktop computer, mobile device, tablet computer, communication device, browser-based device, smartphone, etc. A user at the client device 134 may interact with a user interface component to communicate with the computer system 101. The computer system 101 may act as a server and operate in a networked environment using logical connections to one or more client devices 134.

Figure 2:
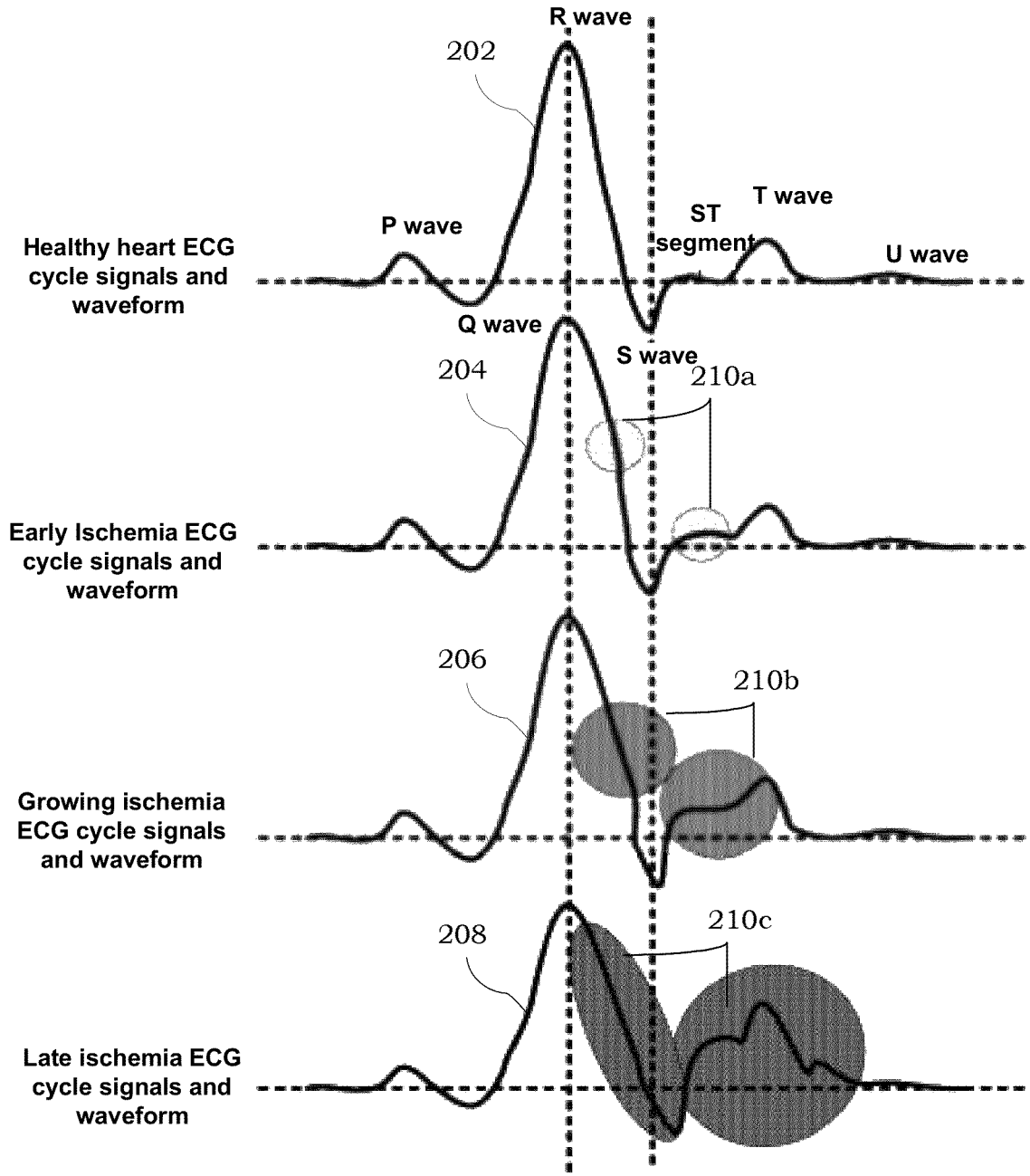
FIG. 2 is a schematic diagram illustrating a comparison of exemplary signal changes in surface ECG waveforms in different kinds of clinical situations.

FIG. 2 is a schematic diagram illustrating a comparison of exemplary signal changes in surface ECG waveforms in different kinds of clinical situations. The first waveform 202 is a normal healthy heart ECG signal waveform; the second waveform 204 is an early ischemia ECG signal waveform; the third waveform 206 is a growing ischemia ECG signal waveform; and the fourth waveform 208 is a late stage ischemia (or early myocardial infarction) ECG signal waveform. Deviations from the normal signal waveform 202 are indicated by circles and ellipses 210a-c that vary in size, color and shape to show abnormality portion, size, severity level, etc. These deviations include R wave amplitude changes, RS waveform changes, S wave latency changes (referring to the R wave point), ST wave changes, T wave morphology and latency changes, etc.

Traditional approaches separate the ECG signal waveform into P wave, QRS complex, ST segment, T wave and U wave (sometimes small or not visible), which are then used to diagnose and characterize atrial and ventricular functions and abnormality. However, such approaches cannot efficiently and effectively detect and characterize ventricular signal changes due to myocardial ischemia and infarction, particularly myocardial tissue malfunctions. For example, some traditional approaches focus only on morphology distortions in the ST segment. However, changes due to the myocardial ischemia in the early fast depolarization activity (QR wave) are not easily detected due to the tissue response frequency and speed limit.

From FIG. 2, it can be observed that morphology distortions also occur in the RS portion and other portions of the T wave portion (210a-c). This provides evidence that the cardiac electrophysiological activities and signal from the peak point of the R wave to the end of the T wave (i.e., later potentials) can be used for myocardial function analysis and detection. By comparing sequential signal cycles of different severity levels (202, 204, 206, 208), it can further be observed that the more severe the myocardial abnormality is, the more distortions (210a-c) there are in the RT portion. Late depolarization response and activity signals (such as RS portions) show significant changes due the myocardial functional abnormality. Late repolarization signals and waveforms, in combination with the ST segment (0.1 mV elevation as the gold clinical standard for myocardial ischemia detection), may also be utilized for myocardial malfunction detection and evaluation.

FIG. 3 illustrates an exemplary waveform segmentation method in accordance with some implementations of the present framework. Ventricular depolarization and repolarization signal activities (or waveform) may be segmented and categorized into several different signal portions: early ventricular repolarization (from R to S wave point), middle ventricular repolarization (from S to T wave point) and late ventricular repolarization (from T to zero voltage crossing). More particularly, the late depolarization and repolarization portions of the ECG signal waveform 302 may be segmented and categorized into various signal portions, such as defined by Table 1. Compared to traditional ECG segmentation methods, the present framework provides more detailed categorization and separation of the patient signals into different functional signal portions. The signal portions may be separated based on the ventricular tissue response sequence and electrophysiological activity speed, fast and slow late potentials.

Table 1 shows exemplary names and definitions of the segmented signal portions. Some signal portion definitions, especially functional definition and combination, may help to discover and highlight ventricular myocardial malfunctions due to low blood flow, ischemia or infarction. For example, a comparison of RS vs. ST portions may facilitate detection of timing duration ratio changes and energy distribution variation during the myocardial ischemia events. Different kinds of signal modes and ratios may be defined based on these segmented signal portions and used to calculate subtle signal morphology changes and distortions due to cardiac pathologies.

Figure 4:
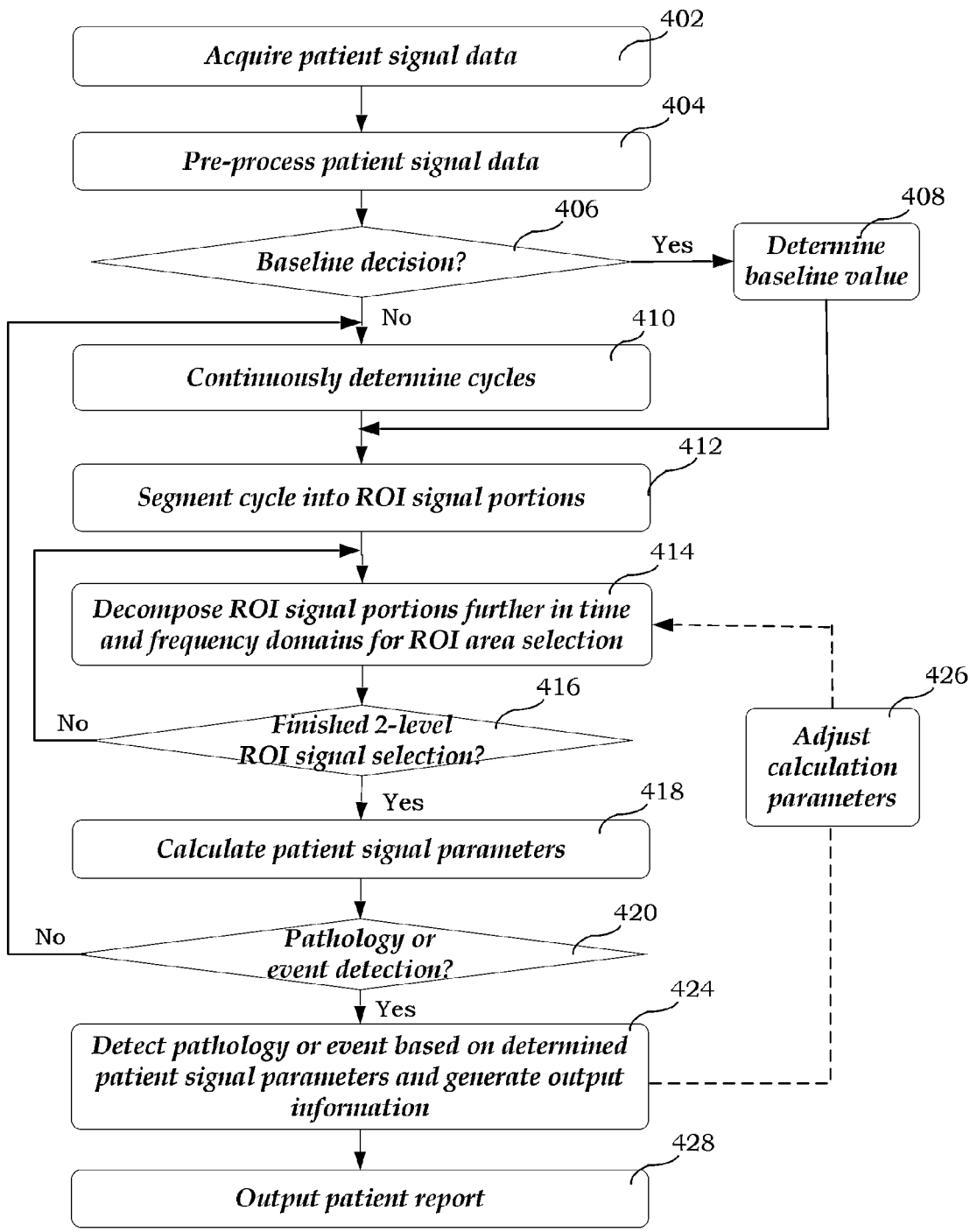
FIG. 4 shows an exemplary method of analyzing patient signals.

FIG. 4 shows an exemplary method 400 of analyzing patient signals. The steps of the method 400 may be performed in the order shown or a different order. Additional, different, or fewer steps may be provided. Further, the method 400 may be implemented with the system 100 of FIG. 1, a different system, or a combination thereof.

At 402, patient monitor 130 acquires patient signal data from a current patient. The patient signal data may be acquired over multiple successive cycles. Such patient signal data may include digitized data of electrophysiological signals, such as ECG or ICEG cardiac signals that indicate electrical activity of a patient's heart over multiple heart cycles. Other types of patient signals, such as hemodynamic (HEMO), oximetric (or SPO2), respiration (or capnographic), other vital sign signals and/or other measurable patient biometric, physiological or medical signals, may also be acquired. In addition, other patient information, such as demographic data, clinical application and patient status, medical history, doctor's experience, may also be acquired. Such patient information may include, but is not limited to, weight, height, gender, age, allergies, medications, etc.

At 404, patient monitor 130 pre-processes the patient signal data. Patient monitor 130 may pre-process the patient signals by filtering, amplification, conditioning, digitization and/or buffering. For example, the patient signals may be pre-filtered and amplified for display on, for instance, patient monitor 130. The patient signals may be filtered to remove patient movement and respiratory artifacts, as well as power line noise. The filter may be adaptively selected in response to data indicating clinical application (e.g. ischemia detection application, rhythm analysis application). In some implementations, patient monitor 130 amplifies, buffers, filters and/or digitizes the patient signals to produce a continuous stream of digitized samples. The digitized patient signal samples or data are provided to patient signal analysis unit 122 for processing.

At 406, patient signal analysis unit 122 determines if a baseline decision is required. A baseline decision is required to determine a baseline value and/or reference signal from the digitized patient signals. The baseline value (or level) generally refers to a known threshold value with which an unknown is compared when measured or assessed, while the reference signal is a benign signal received from a healthy patient. The baseline value of the signal may be a zero voltage line if a static (DC) voltage signal component is filtered out from the signal. The baseline value may be automatically, semi-automatically or manually selected by the user.

If a baseline decision is required, the method 400 continues at 408, wherein the patient signal analysis unit 122 automatically determines the baseline value from the digitized patient signals. The baseline value may comprise a zero voltage line if a static (DC) voltage signal component is filtered out from the signal. The baseline value may be adaptively adjusted according to the current application and clinical requirements.

If no baseline decision is required, the method 400 continues at 410, wherein the patient signal analysis unit 122 continuously determines cycles (e.g., cardiac cycles or heartbeats) from the patient signal data. Cardiac functionality, such as blood flow function in a left ventricle, may be continuously monitored and quantified to enable early detection of clinical events, on-time treatment and/or drug delivery. FIG. 3 shows an exemplary tracing of a cardiac cycle 302 extracted from the patient signal data. As shown, each cardiac cycle 302 may include a P wave, Q wave, R wave, S wave, ST segment, T wave and U wave. Individual cardiac cycles may be identified from the patient signal data.

To determine cycles in the patient signal data, a peak and/or valley detector may be provided in the patient signal analysis unit 122 for detecting the start and end points of a cardiac cycle. The patient signal analysis unit 122 detects cycles of the received patient signal data by detecting peaks within the received data using a peak detector and by segmenting a signal represented by the received data into windows where the cycles are expected and by identifying the peaks within the windows. The start point of a cycle, for example, may be identified by a variety of different methods. In one method, a cycle start point is where the signal crosses the baseline of the signal (in a predetermined wave window, for example). Alternatively, a cycle start point may be a peak or valley of the signal. The patient signal analysis unit 122 may include a timing detector for determining the time duration between the signal peaks and valleys. The time detector may use a clock counter for counting clock cycles between the peak and valley points, and the counting may be initiated and terminated in response to the detected peak and valley characteristics. The area under a determined cycle may be calculated by, for example, numerical integration.

Returning to FIG. 4, at 412, patient signal analysis unit 122 segments an identified cycle into at least two individual regions of interest (ROI). Such segmentation may be performed continuously and in real-time. An ROI signal portion is a graphical deflection commonly observed on a typical electrophysiological signal waveform. The segmentation may be performed automatically by the system in response to data indicating a type of clinical examination being performed, or manually by a user. Different types of ROIs may be identified and selected for signal comparison. In some implementations, at least one of the ROIs is a late potential ROI. A late potential ROI includes an RS, RT, S-full or T-full signal portion of the identified cycle.

Table 1 in FIG. 3 shows exemplary definitions of various different ROI signal portions, including late potential ROIs. The different ROI signal portions may include the RS, ST segment, ST, RT, S-full and/or T-full signal portions. As discussed previously, the ROI signal portions may include a late depolarization signal portion (e.g., RS signal portion) and late repolarization signal portion (e.g., S-full, T-full) that may be used to more efficiently and effectively detect and evaluate myocardial malfunction.

Returning to FIG. 4, at 414, patient signal analysis unit 122 further decomposes the ROI signal portions in time and/or frequency domains. In some implementations, the whole dataset of different ROI signal portions may be used for monitoring cardiac events and tissue function. Alternatively, based on prior knowledge, clinical application and experience, ROI signal portions (e.g., RS, ST) may be decomposed (or separated) in the time and frequency domains into time and frequency ROI areas respectively for signal comparison. Frequency ROI areas are associated with frequency bandwidths (e.g., 20-50 Hz), while time ROI areas are associated with timing durations (e.g., 30 mS window). One or more ROI areas may be selected and pre-determined for signal comparison. The selection may be performed automatically by the system in response to data indicating a type of clinical examination being performed, or manually by a user.

At step 416, patient signal analysis unit 122 determines if the 2-level ROI signal selection is completed. If not, the process 400 continues at 414 to decompose additional ROI signal portions. If so, the process 400 continues at 418 to calculate patient signal parameters based on the selected ROI signal portions and/or areas.

At 418, patient signal analysis unit 122 determines patient signal parameters based on the selected ROI signal portions and/or areas. Such patient signal parameters may include, but are not limited to, timing ratio, integrated amplitude ratio, integrated energy ratio and time-frequency area ratio. These patient signal parameters characterize the mode and pattern changes and distortions within the patient signal waveforms for use in, for example, diagnosing cardiac conditions.

In accordance with some implementations, patient signal analysis unit 122 determines a timing ratio as follows:

$$T\text{-}Ratio_{Time_1 \text{ to } Time_2} = \frac{\text{time\_duration}(\text{Time\_1})}{\text{time\_duration}(\text{Time\_2})} \quad (1)$$

wherein $T\text{-}Ratio_{Time1 \text{ to } Time2}$ represents the timing or signal portion time duration ratio, and Time__1 and Time__2 are two ROI signal portions previously selected in, for example, step 412. A timing detector may be provided in the patient signal analysis unit 122 for determining the time durations of the selected ROI signal portions. The timing detector may use a clock counter for counting a clock between start and end points, and the counting may be initiated and terminated in response to the detected start and end point characteristics.

By comparing timing durations, ventricular tissue functional change and signal distortions may be captured and characterized earlier. Time__1 and Time__2 may be an RS or ST segment, any other signal portion defined in Table 1 of FIG. 3, or a combination of the signal portions defined in Table 1. $T\text{-}Ratio_{Time1 \text{ to } Time2}$ compares the timing of signal time duration, signal latency and signal stretching due to cardiac pathologies, such as low blood flow and excitation of conducting tissue. For example, $T\text{-}Ratio_{RStoST}$ is the time duration ratio for the signal portions between ventricular late depolarization and early repolarization, which can be used to detect the stages of ventricular diseases, such as myocardial ischemia.

In accordance with some implementations, patient signal analysis unit 122 determines an integrated amplitude ratio as follows:

$$AMP\text{-}Ratio_{Time\_1\ to\ Time\_2} = \frac{\int_{i \in Time\_1} A_i(t) dt}{\int_{i \in Time\_2} A_j(t) dt} \quad (2)$$

wherein AMP–Ratio$_{Time\_1\ to\ Time\_2}$ is the integrated amplitude ratio of selected signal portions Time__1 and Time__2. The patient signal analysis unit 122 compares timing ratio T–Ratio$_{Time1\ to\ Time2}$ with integrated amplitude ratio AMP–Ratio$_{Time1\ to\ Time2}$ to evaluate the overall amplitude changes between different signal portions. Polarity of signal amplitude can change in early myocardial ischemia, due to RS portion amplitude decreasing while an ST segment amplitude increases. Hence, the amplitude ratio AMP–Ratio$_{RS\ to\ ST}$ drastically changes during early myocardial ischemia, thereby advantageously facilitating detection of ventricular arrhythmia.

In accordance with some implementations, patient signal analysis unit 122 determines an integrated energy ratio as follows:

$$Energy_A\text{-}Ratio_{Time\_1\ to\ Time\_2} = \frac{\int_{i \in Time\_1} |A_i(t)| dt}{\int_{i \in Time\_2} |A_j(t)| dt} \quad (3)$$

or $$Energy_{A^2}\text{-}Ratio_{Time\_1\ to\ Time\_2} = \frac{\int_{i \in Time\_1} |A_i(t)|^2 dt}{\int_{i \in Time\_2} |A_j(t)|^2 dt} \quad (4)$$

wherein Energy$_A$–Ratio$_{Time\_1\ to\ Time\_2}$ represents a normal energy comparison ratio of absolute amplitude integration, while Energy$_{A^2}$–Ratio$_{Time\_1\ to\ Time\_2}$ represents a squared energy comparison ratio of different selected signal portions Time__1 and Time__2. There may be no polarity consideration for amplitude (positive or negative values) in the calculation of Energy$_A$–Ratio$_{Time\_1\ to\ Time\_2}$ and Energy$_{A^2}$–Ratio$_{Time\_1\ to\ Time\_2}$. This means that when an ischemia event that affects ventricular late depolarization or repolarization occurs, the energy of the ventricular activity distribution changes, especially in response to ventricular energy loss. Therefore, Energy$_A$–Ratio$_{Time\_1\ to\ Time\_2}$ and Energy$_{A^2}$–Ratio$_{Time\_1\ to\ Time\_2}$ facilitates determining energy distribution changes due to ventricular arrhythmia.

In accordance with some implementations, patient signal analysis unit 122 determines an integrated time frequency area ratio as follows:

$$Time\text{-}Freq\text{-}Area_A\text{-}Ratio_{Time\_1\ to\ Time\_2} = \frac{\int\int_{i \in Time\_1, t \in \Phi; f \in \Theta} |A_i(t,f)| dt df}{\int\int_{i \in Time\_2, t \in \Phi; f \in \Theta} |A_j(t,f)| dt df} \quad (5)$$

or $$Time\text{-}Freq\text{-}Area_{A^2}\text{-}Ratio_{Time\_1\ to\ Time\_2} = \frac{\int\int_{i \in Time\_1, t \in \Phi; f \in \Theta} |A_i(t,f)|^2 dt df}{\int\int_{i \in Time\_2, t \in \Phi; f \in \Theta} |A_j(t,f)|^2 dt df} \quad (6)$$

wherein Time–Freq–Area$_A$–Ratio$_{Time\_1\ to\ Time\_2}$ and Time–Freq–Area$_{A^2}$–Ratio$_{Time\_1\ to\ Time\_2}$ represent time-frequency area ratios (normal absolute amplitude and squared amplitude integration) between two segmented signal portions, Time__1 and Time__2; A(t, f) represents the amplitude value of the respective signal portion at specific time t and frequency f, $\Phi$ is the timing dataset of the ROI time duration and timing ranges; and $\Theta$ is the frequency dataset of the ROI frequency ranges, such as 10-20 Hz, 30-45 Hz. By decomposing the ROI signal portions into different ROI areas (e.g., 10-20 Hz and 30 mS window), time-frequency ranges in the signal portions may be selected and compared. The time-frequency-based energy of specific time duration and frequency ranges may be used to detect myocardial ischemia events and pathologies.

In some implementations, time and frequency joint distribution-based area selection with specific time duration and frequency ranges in a ROI of a signal portion detects and indicates severity of a specific type of cardiac arrhythmia. In one example for left anterior descending coronary artery (LAD) myocardial ischemia detection, in a late ventricular depolarization signal portion RS, a time area of RS signal from R wave may be 5-15 ms while frequency areas of RS signal may be 5-10 Hz, 20-45 Hz, 100-200 Hz. Similarly, the ST portion (see FIG. 3) for LAD ischemia analysis may include time portions (from S point) of 1-15 ms and 20-60 mS, and frequency portions of 15-20 Hz, 25-35 Hz, and 45-60 Hz. By comparing these ROI areas of such time-frequency ranges between the RS and ST portions in the cardiac signal, LAD myocardial ischemia may be detected and characterized.

At 420, patient signal analysis unit 122 determines if pathology or event detection is to be automatically performed. If not, the method 400 returns to step 410 to continuously process cardiac cycles. If yes, the method 400 continues to 424.

At 424, patient signal analysis unit 122 detects pathology or event based at least in part on the determined patient signal parameters. Such pathology or event may be characterized with attributes, such as cardiac abnormality severity, location, type, pattern, trend, and so forth. Other output information, such as patient heath status, treatment priority, treatment methods and associated treatment control parameter selections (e.g., ablation timing, pacing mode, pacing amplitude and energy level, pulse duration, defibrillation position and energy level, etc.), cause analysis and mapping results, may also be derived at least in part from the patient signal parameters.

In some implementations, the determined patient signal parameters and/or other input patient data are linearly or non-linearly combined to generate the patient health status, treatment suggestions, and/or other types of output information. Different methods, such as an artificial neural network (ANN), fuzzy algorithm, etc., may be used to integrate the input patient data.

Figure 5:
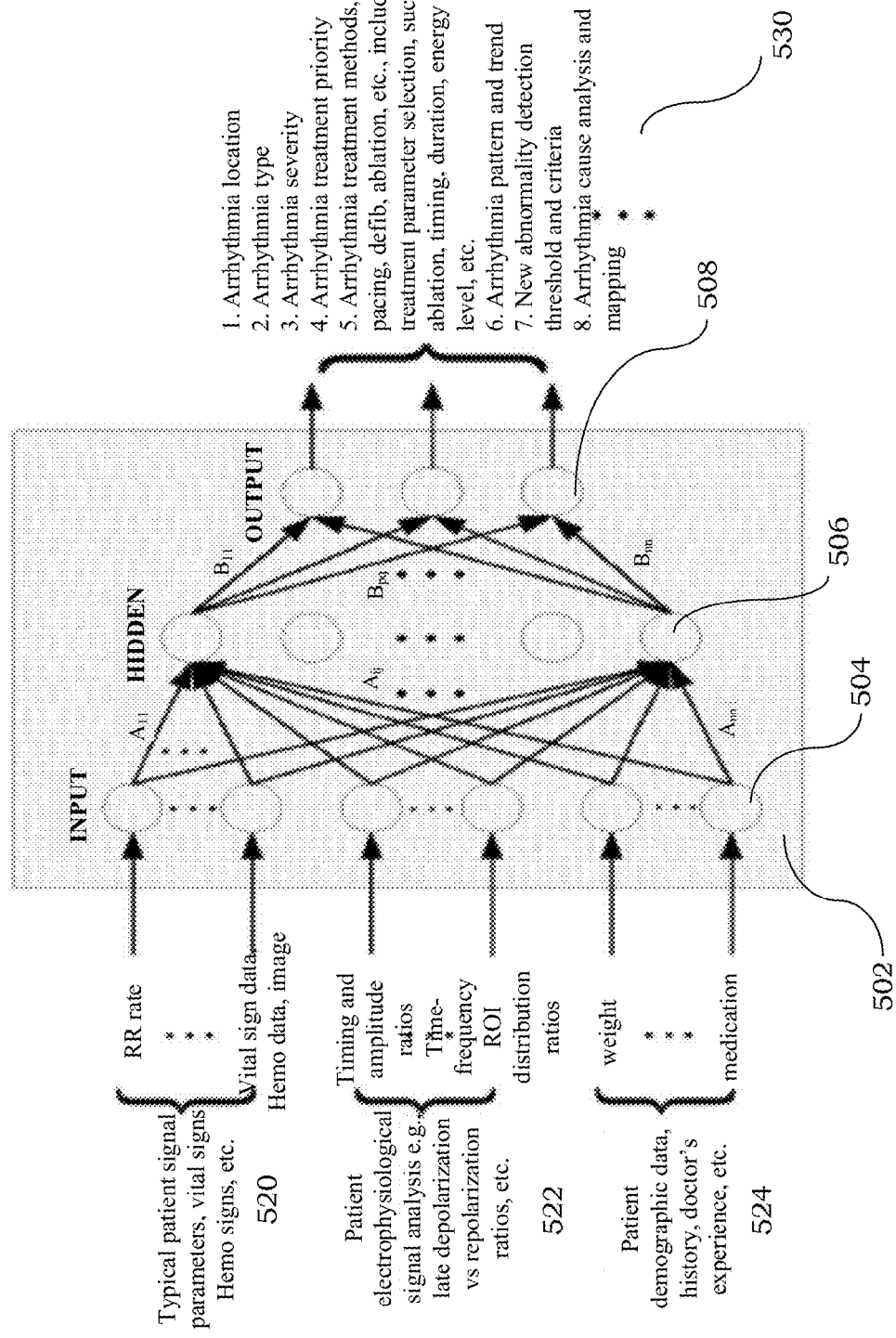
FIG. 5 shows an exemplary artificial neural network (ANN) structure.

FIG. 5 shows an exemplary ANN structure 502 for cardiac segmented ventricular activity signal analysis and adaptive and automatic data fusion. The ANN structure 502 integrates multiple types of input patient data for providing decision support in diagnosis and treatment of cardiac pathologies, arrhythmia, and analysis of tissue function. Exemplary ANN structure 502 includes three layers—input layer 504, hidden layer 506 and output layer 508—for combining and integrating different kinds of acquired patient signal data (e.g., vital sign, HEMO sign data, blood pressure, SPO2, images, signal waveforms, different signal calculation ratios, etc.) 520, determined patient signal parameters (e.g., late depolarization and repolarization timing and/or amplitude ratios, time-frequency ROI distribution ratios, etc.) 522, and patient demographic data, medical history, doctor's experience and other patient information (e.g., weight, height, medication, allergies, etc.) 524.

ANN structure 502 combines and maps input patient data 520, 522 and 524 to output parameters 530 for use in quantitative and qualitative diagnosis and treatment of emerging arrhythmia events. Output parameters 530 may indicate, for example, estimated abnormality or pathology (e.g., arrhythmia) location, type, severity, pattern, and/or trend, treatment priority, suggestions for methods of treatment (e.g., pacing, defibrillation ablation, etc.) and associated treatment control parameter selections (e.g., ablation, timing, duration, energy level, etc.), prediction of cardiac pathological trends, suggestions for further treatment indication and medication, calculation control parameters (e.g., new abnormality detection threshold and criteria), abnormality cause analysis and mapping results, cardiac rhythm management (CRM), and so forth. Such output parameters 530 may be used for the detection, diagnosis, warning and/or treatment of abnormalities. They may be used in different clinical applications, such as in operating room (OR) monitoring, ICU/CCU critical monitoring and emergency room (ER) patient status and health monitoring.

$A_{ij}$ are weights applied between the input layer 504 and the hidden layer 506, while $B_{pq}$ are weights applied between the hidden layer 506 and the output layer 508 of the ANN computation. $A_{ij}$ weights and $B_{pq}$ weights are adaptively adjusted and tuned using a training data set. ANN unit 502 may incorporate a self-learning function that processes new input data 520, 522 and 524 to increase the precision and accuracy of calculated results. The exemplary ANN-based analysis may combine patient signal parameters with information derived from a medical professional's experience (input and suggested controlling mode) to greatly improve the sensitivity, specificity, stability and reliability of non-invasive methods.

Turning back to FIG. 4, at 426, patient signal analysis unit 122 may optionally adaptively adjust calculation parameters used for calculating the parameters described herein. The adaptive adjustment may be performed automatically, semi-automatically or manually by the clinical user. Such calculation parameters include, but are not limited to, severity threshold, calculation time step, signal portion, ROI area, and so forth.

At 428, patient signal analysis unit 122 outputs a patient report. The patient report may indicate the abnormality, associated characteristics (e.g., type, severity, timing, etc.) and other output information (e.g., suggested treatment options). The patient report may be electronically shared or transmitted to client device 134 in the form of, for example, a warning message, recording or report. The patient report may also be printed and distributed to relevant parties. Further, the patient report may also be stored in database 124 for future retrieval.

Figure 6:
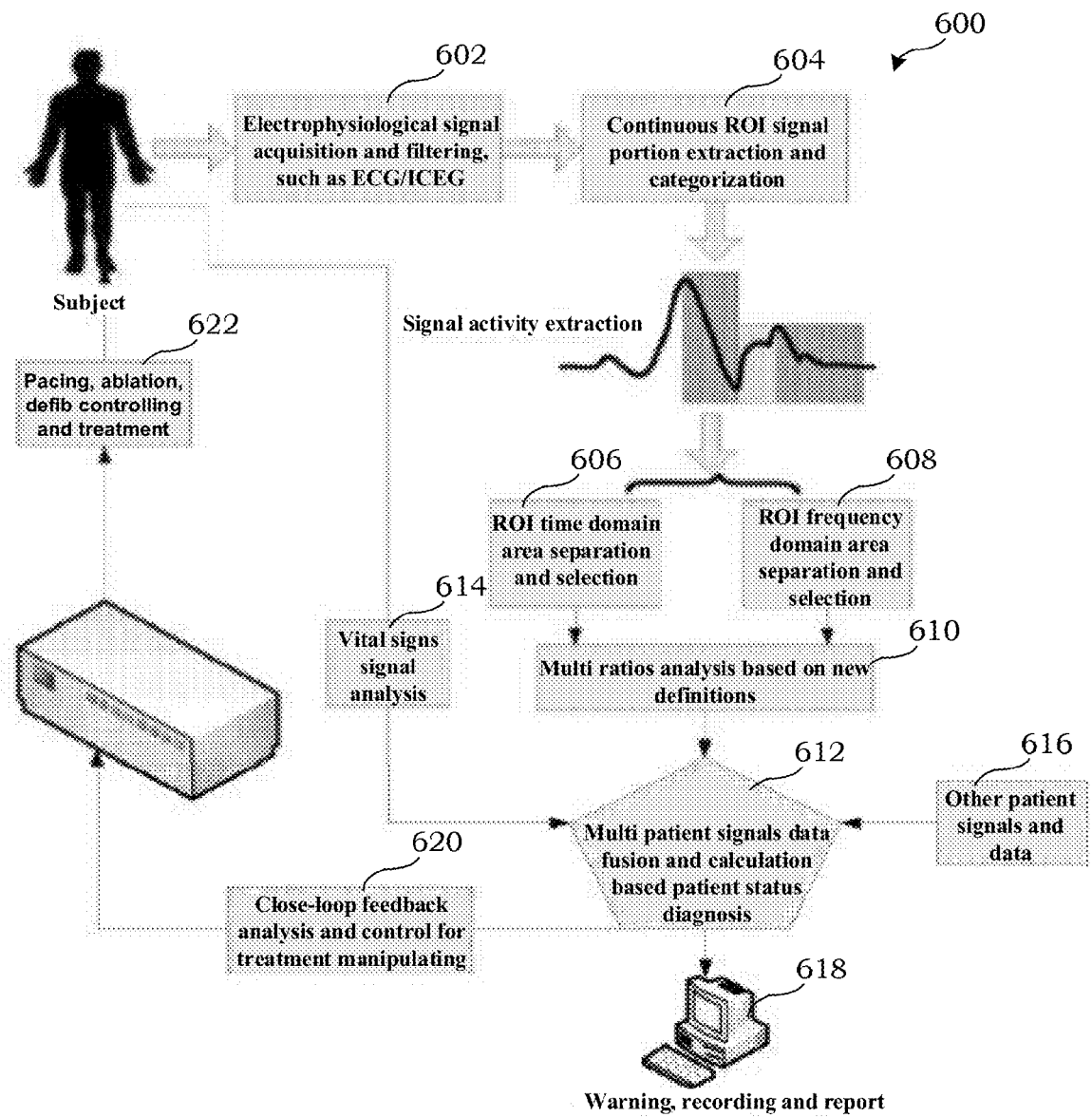
FIG. 6 shows an exemplary workflow for automated closed-loop system feedback control.

FIG. 6 shows an exemplary workflow 600 for automated closed-loop system feedback control. At 602, electrophysiological signal data is acquired and filtered. The electrophysiological signal data may be, for example, surface ECG or intra-cardiac electrograms from multiple-channels or leads. As discussed previously, there may be two levels of ROI analysis: (1) ROI signal portion extraction, categorization and selection of continuous electrophysiological signal data (604); (2) ROI time domain and/or frequency domain area separation and selection (606 and 608). At 610, different patient signal parameters may be determined based on the selected ROI signal portions and/or areas. At 612, the determined patient signal parameters may be combined with other patient data, such as vital sign signal analysis results 614 and other patient signals and data 616 to generate output patient status information (e.g., warning, recordings, reports) 618.

At 620, the determined patient signal parameters are used to adaptively adjust and manipulate treatment control parameters of medical devices. This automatic closed-loop, adaptive control and treatment based on late depolarization vs. repolarization analysis may be applied to an implantable cardioverter defibrillator (ICD) device, such as a cardioverter and pacemaker. Such medical devices are used to perform, for example, pacing, ablation, defibrillation, treatment, etc. at 622.

Figure 7:
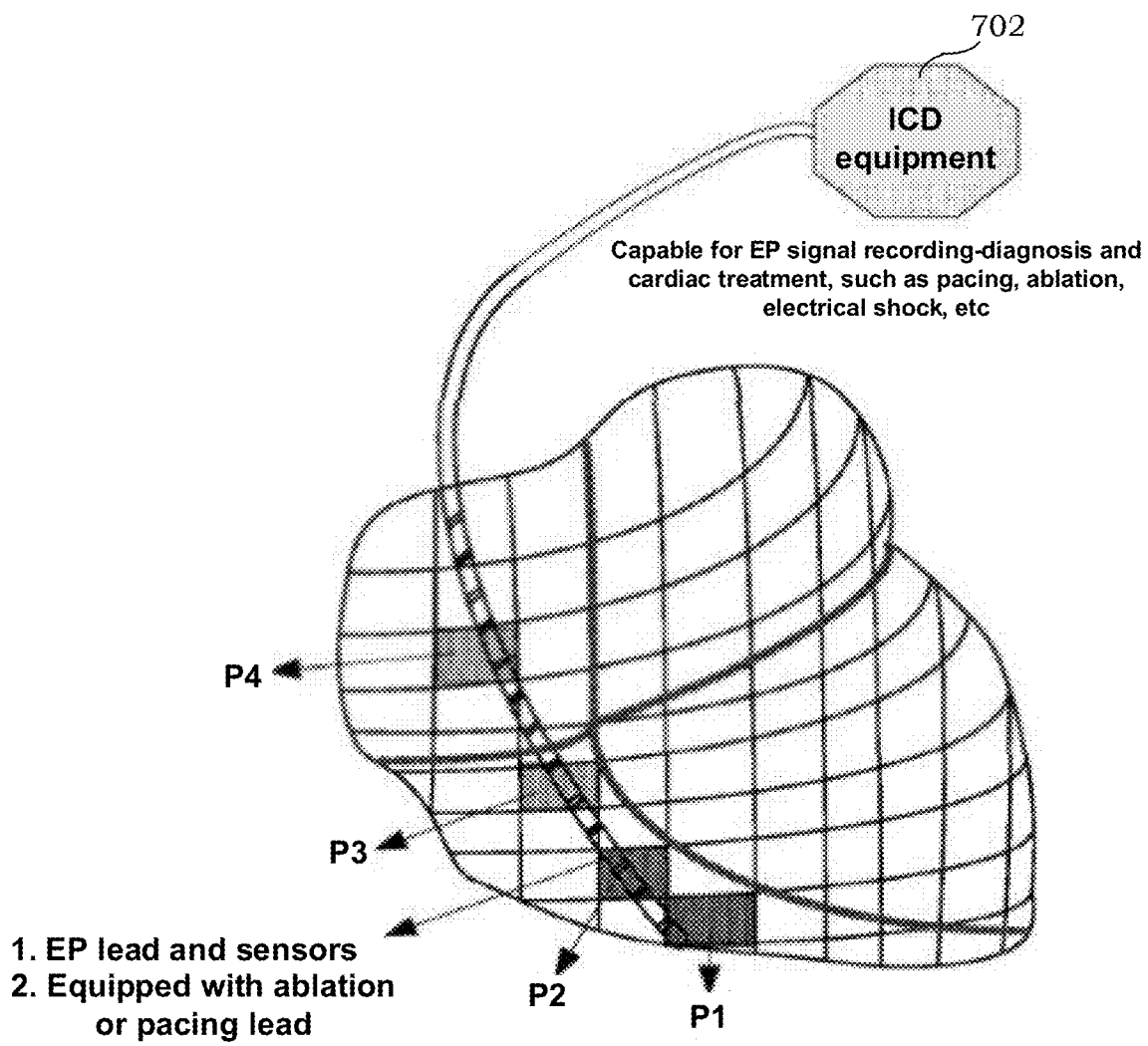
FIG. 7 shows an exemplary implantable cardioverter defibrillator (ICD) cardiac rhythm control device.

FIG. 7 shows an exemplary ICD cardiac rhythm control device 702 that provides multi-lead electrogram signal and waveform ratio analysis. The exemplary ICD monitoring device 702 may determine ventricular late depolarization and repolarization signal ratios, calculate and analyze patterns and modes based on such ratios, as well as known signal analysis, such as ST segment voltage elevation analysis. There are multichannel sensors and transducers in the device 702, which capture real-time cardiac electrophysiological function activities and enable cardiac status mapping. The ICD device 702 may perform real-time online treatment, using pacing rate-pulse duration control, or ablation parameter control. As shown, analysis based on 4 different leads (positions P1, P2, P3, P4) is used to achieve cardiac arrhythmia mapping (e.g., location, severity, treatment priorities) of ventricular tissue.

FIG. 8 shows a table 802 for comparing exemplary multi-channel signal changes for myocardial ischemia diagnosis. Normal cardiac rhythm, early ischemia and early infarction (late ischemia) episodes are shown. An ST segment elevation computed using a standard method and a time-frequency distribution area ratio (Time–Freq–Area$_{A^2}$–Ratio$_{RS\ to\ T\text{-}full}$) determined using some implementations of the present framework were used for comparison. For the Time–Freq–Area$_{A^2}$–Ratio$_{RS\ to\ T\text{-}full}$ ratio, the signal time range was about 5-25 ms (from R wave peak time) for the RS signal portion (late depolarization) and the time range for the T-full signal portion was about 0-75 ms (from S wave point); the frequency range was about 25-50 Hz for the RS signal portion and 10-25 Hz for the T-full signal portion.

Continuous monitoring and calculation of the signal from different positions along the catheter of an ICD device may be used for real time diagnosis and treatment. In Table 802, it can be observed that location P2 shows a greater signal change than locations P1, P3 and P4, which means P2 is the highest priority point for electrical ablation. Using the standard method, especially for P2, ST segment elevation voltage change is only 0.01 mV for an early ischemia event and 0.08 mV for late ischemia, which does not exceed a 0.1 mV warning threshold. The time-frequency ROI distribution area ratio (Time–Freq–Area$_{A^2}$–Ratio$_{RS\ to\ T\text{-}full}$), on the other hand, shows more than 100% value change for early ischemia and more than 200% value change for late ischemia. This indicates that the segmented ventricular signal portion ratio effectively facilitates detection and characterization of ventricular ischemia events. Different kinds of test and probability analysis may further help to identify cardiac arrhythmias.

Additionally a multi-channel signal energy calculation may be applied in 2-dimensional and 3-dimensional heart mapping for real-time cardiac function diagnosis (signal energy mode vs. time). By using multi-channel signal energy distribution information mapping, the abnormal tissue location, potential abnormal pathway, arrhythmia severity, etc., may be visually mapped. The cardiac signal energy distribution determination may use different kinds of input electrophysiological signals, such as ICEG signals (intra-cardiac electrograms) and hemodynamic pressure signals (e.g., IBP, NIBP signals, cardiac output signals, etc.).

While the present invention has been described in detail with reference to exemplary embodiments, those skilled in the art will appreciate that various modifications and substitutions can be made thereto without departing from the spirit and scope of the invention as set forth in the appended claims. For example, elements and/or features of different exemplary embodiments may be combined with each other and/or substituted for each other within the scope of this disclosure and appended claims.

The invention claimed is:

1. A non-transitory computer readable medium embodying a program of instructions executable by machine to perform steps for patient signal analysis, the steps comprising:
receiving patient signal data including at least one identified cardiac cycle;
segmenting the cardiac cycle into at least two regions of interest, wherein at least one of the at least two regions of interest is a late potential region of interest;
decomposing the at least two regions of interest in time and frequency domains to generate time and frequency signal areas;
determining at least one patient signal parameter based at least in part on the regions of interest or signal areas; and
detecting a cardiac pathology or event based on the determined at least one patient signal parameter.

2. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest is an RS, RT, S-full or T-full signal portion, and wherein the at least two regions of interest comprise different late potential regions of interest;
determining at least one patient signal parameter based at least in part on the segmented regions of interest; and
detecting a pathology or event based on the determined at least one patient signal parameter.

3. The system of claim 2 wherein the patient signal data comprises electrophysiological signal data that indicate electrical activity of a patient's heart over multiple cardiac cycles.

4. The system of claim 2 wherein the at least two regions of interest comprises an ST segment or ST signal portion.

5. The system of claim 2 wherein the late potential region of interest comprises an RS signal portion that characterizes late depolarization of the cycle.

6. The system of claim 2, wherein the processor is further operative with the computer readable program code to decompose the at least two regions of interest in time domain into a time signal area associated with a timing duration.

7. The system of claim 6, wherein the processor is further operative with the computer readable program code to decompose the at least two regions of interest in frequency domain into a frequency signal area associated with a frequency bandwidth.

8. The system of claim 7 wherein the patient signal parameter comprises a time-frequency area ratio of the regions of interest.

9. The system of claim 2, wherein the processor is operative with the computer readable program code to determine the pathology or event by combining, via an artificial neural network, the determined patient signal parameter with other input patient data.

10. The system of claim 2, wherein the processor is further operative with the computer readable program code to adaptively adjust one or more calculation parameters based on the determined patient signal parameter.

11. The system of claim 2, wherein the processor is further operative with the computer readable program code to adaptively adjust one or more treatment control parameters of a medical device based on the determined patient signal parameter.

12. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest comprises an RT signal portion that is defined from a peak time of ventricular depolarization of the cycle to a peak time of ventricular repolarization of the cycle;
determining at least one patient signal parameter based at least in part on the segmented regions of interest; and
detecting a pathology or event based on the determined at least one patient signal parameter.

13. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest comprises an S-full signal portion that characterizes functional full ventricular repolarization and later potentials of the cycle including a U wave;
determining at least one patient signal parameter based at least in part on the segmented regions of interest; and
detecting a pathology or event based on the determined at least one patient signal parameter.

14. A system for patient signal analysis, comprising:
a non-transitory memory device for storing computer readable program code; and a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest comprises a T-full signal portion that characterizes functional full repolarization and later potentials of the cycle including a U wave;
determining at least one patient signal parameter based at least in part on the segmented regions of interest; and
detecting a pathology or event based on the determined at least one patient signal parameter.

15. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest is an RS, RT, S-full or T-full signal portion;
determining at least one patient signal parameter based at least in part on the segmented regions of interest; and
detecting a pathology or event based on the determined at least one patient signal parameter, wherein the patient signal parameter comprises a timing ratio of the regions of interest.

16. The system of claim 15 wherein the regions of interest comprise an RS signal portion and an ST signal portion.

17. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest is an RS, RT, S-full or T-full signal portion;
determining at least one patient signal parameter based at least in part on the segmented regions of interest; and
detecting a pathology or event based on the determined at least one patient signal parameter, wherein the patient signal parameter comprises an integrated amplitude ratio of the regions of interest.

18. The system of claim 17 wherein the regions of interest comprise an RS signal portion and an ST signal portion.

19. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest is an RS, RT, S-full or T-full signal portion;
determining at least one patient signal parameter based at least in part on the segmented regions of interest and by determining a timing ratio and an integrated amplitude ratio of the regions of interest; and
detecting a pathology or event based on the determined at least one patient signal parameter.

20. A system for patient signal analysis, comprising:
a non-transitory memory device for storing computer readable program code; and
a processor in communication with the memory device, the processor being operative with the computer readable program code to perform steps comprising:
receiving patient signal data including at least one identified cycle;
segmenting the cycle into at least two regions of interest including a late potential region of interest, wherein the late potential region of interest is an RS, RT, S-full or T-full signal portion;
determining at least one patient signal parameter based at least in part on the segmented regions of interest; and
detecting a pathology or event based on the determined at least one patient signal parameter, wherein the patient signal parameter comprises an integrated energy ratio of the regions of interest.

21. A method of patient signal analysis, comprising:
receiving patient signal data including at least one identified cycle;
segmenting the cycle into at least two regions of interest including a late potential region of interest, wherein the late potential region of interest is an RS, RT, S-full or T-full signal portion, and wherein the at least two regions of interest comprise different late potential regions of interest;
determining at least one patient signal parameter based at least in part on the segmented regions of interest; and
detecting a pathology or event based on the determined at least one patient signal parameter.

* * * * *